(12) United States Patent
Swider

(10) Patent No.: US 7,205,152 B2
(45) Date of Patent: *Apr. 17, 2007

(54) CLOSED LOOP SYSTEM AND METHOD FOR AIR SAMPLING OF MAIL PRODUCTS

(75) Inventor: John T. Swider, Port Crane, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 483 days.

This patent is subject to a terminal disclaimer.

(21) Appl. No.: 10/201,169

(22) Filed: Jul. 22, 2002

(65) Prior Publication Data

US 2003/0124027 A1 Jul. 3, 2003

Related U.S. Application Data

(60) Provisional application No. 60/344,848, filed on Dec. 31, 2001.

(51) Int. Cl.
G01N 33/00 (2006.01)
G01N 33/22 (2006.01)

(52) U.S. Cl. .............. 436/1; 436/2; 436/86; 436/104; 436/175; 422/83; 422/119; 73/12.04; 73/23.2; 73/28.01

(58) Field of Classification Search .......... 436/1, 436/174, 2, 43, 86, 175, 104; 422/61, 83, 422/119; 73/28.01, 12.04, 31.03, 23.2
See application file for complete search history.

(56) References Cited

U.S. PATENT DOCUMENTS 3,661,256 A    5/1972   Hain ........................ 209/74
3,915,339 A   10/1975   Matson
3,998,101 A   12/1976   Bradshaw et al.
4,580,440 A    4/1986   Reid et al.
4,718,268 A    1/1988   Reid et al.
4,764,351 A    8/1988   Hennebert et al.
4,786,295 A   11/1988   Newman et al. ............. 55/213
4,987,767 A    1/1991   Corrigan et al.
5,009,869 A    4/1991   Weinberg et al. ........... 423/210
5,109,691 A    5/1992   Corrigan et al.
5,225,167 A    7/1993   Wetzel ..................... 422/121
5,322,603 A    6/1994   Kameda
5,325,795 A    7/1994   Nelson et al. .............. 110/236

(Continued)

OTHER PUBLICATIONS

International Search Report, Oct. 21, 2003, PCT/US02/34375 (12078-197PCT) WO 03/081214, Published PCT International Application, Publication Date Oct. 2, 2003, PCT/US02/34375 (12078-197PCT).

(Continued)

Primary Examiner—Lyle A. Alexander
(74) Attorney, Agent, or Firm—Burns & Levinson LLP; Jacob N. Erlich; Harvey Kaye

(57) ABSTRACT

A self-contained closed loop system and method for detecting contaminants in, on, and around objects. The system includes an air duct subsystem connecting at least one sensor to a sealed housing containing a rotating container. Air from the sealed housing is circulated past a sensor to detect, for example, biological or chemical contaminants. If a contaminant is detected, an indicator is set and a contaminant neutralizer is optionally injected into the air duct subsystem.

18 Claims, 11 Drawing Sheets

U.S. PATENT DOCUMENTS

| | | | |
|---|---|---|---|
| 5,345,809 A | 9/1994 | Corrigan et al. | |
| 5,465,607 A | 11/1995 | Corrigan et al. | |
| 5,470,546 A | 11/1995 | Hall | |
| 5,505,904 A | 4/1996 | Haidinger et al. | 422/24 |
| 5,585,575 A | 12/1996 | Corrigan et al. | |
| 5,591,117 A | 1/1997 | Zelno | |
| 5,700,426 A | 12/1997 | Schmitthaeusler et al. | |
| 5,833,740 A | 11/1998 | Brais | 96/16 |
| 5,841,038 A | 11/1998 | Volz | |
| 5,859,362 A | 1/1999 | Neudorfl et al. | |
| 5,942,699 A | 8/1999 | Ornath et al. | |
| 6,041,669 A | 3/2000 | Brassell et al. | 73/864.74 |
| 6,062,977 A | 5/2000 | Hague | 454/341 |
| 6,074,608 A | 6/2000 | Matz | 422/83 |
| 6,159,422 A | 12/2000 | Graves et al. | |
| 6,183,950 B1 | 2/2001 | Madonna et al. | |
| 6,199,604 B1 | 3/2001 | Miyajima | 141/98 |
| 6,233,748 B1 | 5/2001 | Gieger et al. | 2/410 |
| 6,295,860 B1 | 10/2001 | Sakairi et al. | |
| 6,324,927 B1 | 12/2001 | Ornath et al. | |
| 6,742,703 B2 | 6/2004 | Esakov et al. | |
| 6,792,795 B2 * | 9/2004 | Jones et al. | 73/37 |
| 2001/0029793 A1 | 10/2001 | Moler et al. | 73/863.22 |
| 2002/0124664 A1 | 9/2002 | Call et al. | |
| 2002/0126008 A1 | 9/2002 | Lopez et al. | |
| 2003/0086821 A1 | 5/2003 | Matthews | 422/29 |
| 2003/0222132 A1 | 12/2003 | Esakov et al. | |
| 2004/0026491 A1 * | 2/2004 | Beckert et al. | 232/17 |

OTHER PUBLICATIONS

WIPO International Patent Application Publication No. WO 98/57140, "Method and Apparatus for Sampling Contaminants", Publication Date: Dec. 17, 1998.

European Patent Application Publication No. EP 0169057, "Method and Apparatus for Detecting a Contraband Substance", Publication Date: Jan. 22, 1986.

U.S. Appl. No. 60/344,848, filed Dec. 31, 2001, John T. Swider.

U.S. Postal Service Emergency Preparedness Plan for Protecting Postal Employees and Postal Customers from Exposure to Biohazardous Material and for Ensuring Mail Security Against Bioterror Attacks; Mar. 6, 2002; publiished by USPS.

* cited by examiner

CLOSED LOOP SYSTEM AND METHOD FOR AIR SAMPLING OF MAIL PRODUCTS

CROSS REFERENCE TO RELATED APPLICATIONS

The present application claims priority to U.S. Provisional Patent Application No. 60/344,848 filed Dec. 31, 2001, entitled CLOSED LOOP SYSTEM FOR AIR SAMPLING OF CONTAINED MAIL PRODUCTS which is incorporated herein by reference.

BACKGROUND OF THE INVENTION

This invention relates generally to the containment and detection of hazardous material in a sealed container, and, more particularly to a closed loop system to recirculate air over or through items contained in a sealed container.

The recent incidents of anthrax-laced letters flowing through the United States Postal Service (USPS) facilities have alarmed the nation and the world. Currently, the tainted letters are discovered after the recipient accepts delivery or by alert postal employees noticing white powder that could be anthrax on mail parcels, sorting and distribution equipment, or themselves. There appear to be no current security devices or procedures that are available to intercept such letters at the earliest source of introduction into the USPS system, for example at the mailbox or post office drop box. Also, there appears to be no known device or procedure that safeguards against biological agents in powdery forms such as anthrax.

Current devices that could detect and safeguard against biological agents can present further problems such as introducing additional contaminants into the air sample that may cause false alarms or shorten the life span of contaminant detection devices. Some current devices are deficient in that they allow the migration of deadly contaminants to the outside environment, or they require the use of costly high efficiency particle air filters (HEPA) filters to process air before release to the outside environment. Some lack the capability to interject a contaminant neutralizer into a sealer container when a contaminant has been detected.

A system is needed in which detection and neutralization of mail- and parcel-born contamination can happen in a closed environment without manual intervention.

SUMMARY OF THE INVENTION

The problems set forth above as well as further and other problems are solved by the present invention. The solutions and advantages of the present invention are achieved by the illustrative embodiment of the present invention described hereinbelow.

The present invention is a self-contained closed loop system and method for detecting contaminants in and around objects, including mail pieces and parcels, and neutralizing the environment containing the contaminants. The system of the present invention includes, but is not limited to, a housing such as a cabinet, a perforated container, an air duct subsystem, a power subsystem, a sensor subsystem, an indicator subsystem, and a controller. Optionally, the system of the present invention can include a blower subsystem and a neutralization mechanism.

The housing creates an enclosure and forms an airflow barrier between the enclosure and the outside ambient air. The housing has a housing opening for inserting and removing the object(s). The container forms a cavity for holding the object(s). The container has a shell with at least one perforation and is rotatably mounted within the housing. The container has at least one container opening for inserting and removing the object(s). The power subsystem, operably connected to the container, rotates the container.

The sensor subsystem tests an air stream for contaminants. The indicator subsystem is operably connected to the sensor subsystem and provides a signal when at least one contaminant is detected.

The air duct subsystem is capable of ducting the air stream in a closed loop throughout the system. The air duct subsystem can duct the air stream into a perforated pipe that is mounted within the container. The perforated pipe allows the air stream to enter the cavity, and the perforation(s) in the cavity allows the air stream to enter the enclosure. The air duct subsystem can receive the air stream from the enclosure and can duct it past the sensor subsystem and back through the housing into the container, optionally forced by the blower subsystem.

The controller sequences operations among the sensor subsystem and the power subsystem so that particles that can be emitted while the object(s) are being tumbled within the cavity when the container is rotating. The particles can pass through the perforation(s) in the container from the cavity to the housing and then are entrained with the air stream into the air duct subsystem. The air stream and particles exit the housing and are ducted past the sensor subsystem which sends a signal to the indicator subsystem if contaminant(s) is detected in the particles.

Optionally, the blower subsystem can force the air stream through the air duct subsystem. If a blower subsystem is used to force the air stream, the controller can sequence activities among the blower subsystem, the sensor subsystem, and the power subsystem. Also optionally, when contaminant(s) is detected, a neutralization mechanism can inject a conventional contaminant neutralizer such as chlorine-calcium, formalin, or lye solutions into the air stream in the air duct subsystem. If a neutralization mechanism is used, the controller can sequence activities among the neutralization mechanism, the sensor subsystem, and the power subsystem, and optionally the blower subsystem.

The method of the present invention includes the steps of loading a perforated container with at least one object, enclosing the perforated container within a housing, and sealing the housing. In this method, the step of sealing forms an ambient air barrier which prevents air and particles emitted from the perforated container into the housing from entering the ambient air outside the housing. The method of the present invention further includes the step of rotating the perforated container. Rotation of the perforated container that contains objects can serve to release particles that are on and in the objects within the perforated container into an air stream that entrains emitted particles. The method further includes the step of sampling the air stream that enters the housing through the perforations in the container. The method includes the steps of testing for at least one contaminant and providing an indicator if at least one contaminant is detected. The method can optionally include the steps of forcing air into the rotating perforated container, which in turn is forced through the perforations into the housing, and introducing a neutralizing agent into the air stream if the air stream contains at least one contaminant.

For a better understanding of the present invention, together with other and further objects thereof, reference is made to the accompanying drawings and detailed description. The scope of the present invention is pointed out in the appended claims.

DETAILED DESCRIPTION OF THE INVENTION

The present invention is now described more fully hereinafter with reference to the accompanying drawings, in which the illustrative embodiment of the present invention is shown.

Figure 1:
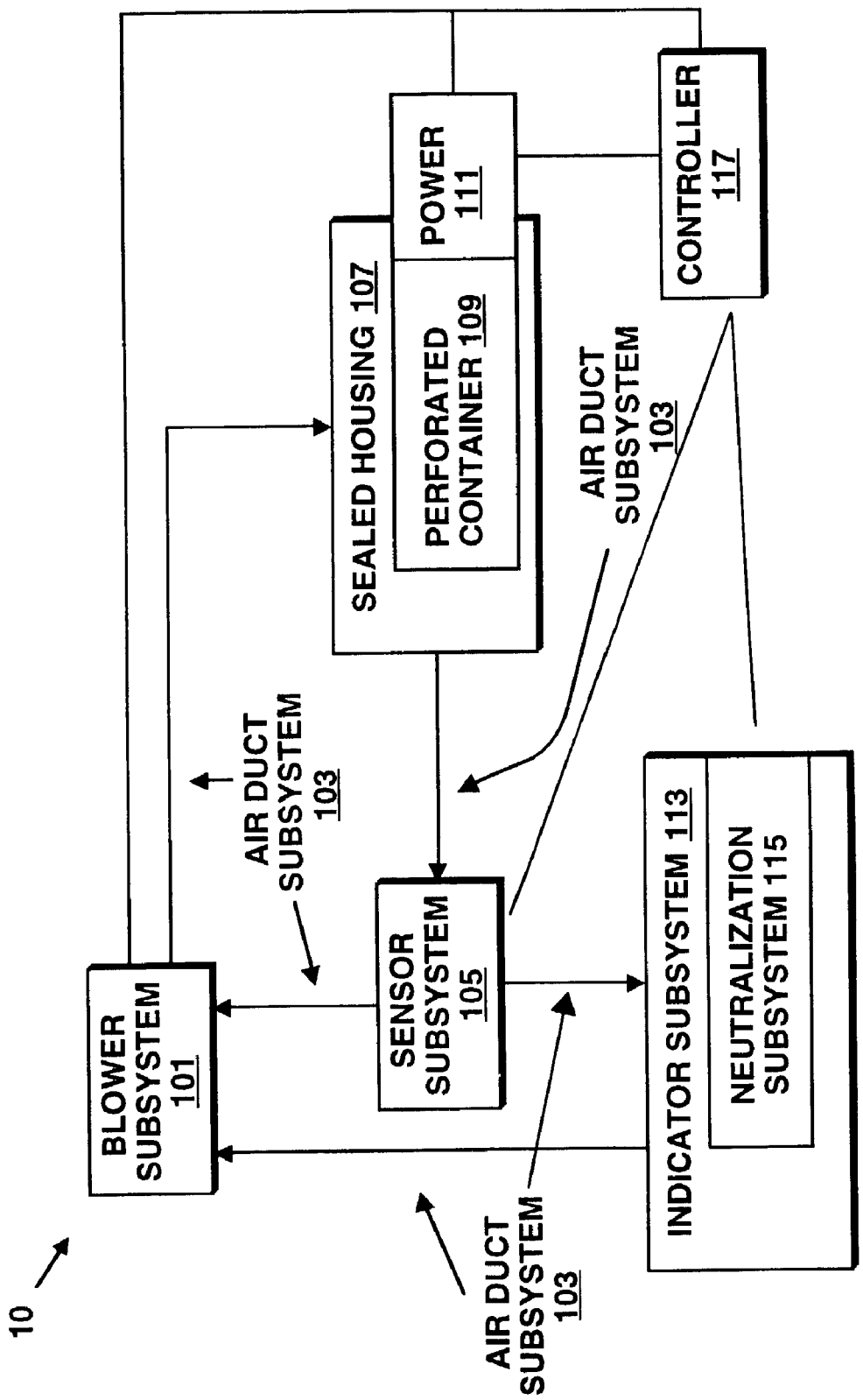
FIG. 1 is a schematic block diagram of the components of the system of the present invention.

System 10 of the present invention, shown in FIG. 1, includes, but is not limited to, a sealed housing 107 forming an enclosure, the enclosure containing a perforated container 109 forming a cavity, a sensor subsystem 105, and an indicator subsystem 113. Optionally, system 10 can include a blower subsystem 101. Components 101, 105, and 107 are in airflow communication through air duct subsystem 103. In addition, a power subsystem 111, an optional neutralization mechanism 115, and a controller 117 complete system 10.

In operation, perforated container 109 is rotated by power subsystem 111 while optional blower subsystem 101 forces an air stream through air duct subsystem 103. When perforated container 109 is loaded with objects, such as mail pieces and/or parcels, and rotated, any loose particles that are on or in the objects can be released. These particles can eventually be forced into the enclosure formed by the sealed housing 107 through the perforations in perforated container 109 by the pressure of air flowing into the perforated container 109 and by the container's centrifugal force. The particles can then be entrained into the air stream that is flowing into sealed housing 107 from the perforations in perforated container 109. This air stream is ducted by the air duct subsystem 103 past sensor subsystem 105 where it is tested by conventional sensor equipment such as the BIONI or Biological Aerosol Real Time Sensors manufactured by Pacific Scientific Instruments and the Biological Aerosol Warning Systems I, developed by the assignee of this application, or any cost-effective, real-time sensor for airborne biological particles or other contaminants. If contaminants are detected, indicator subsystem 113 provides an indication of the presence of contaminants. Optionally, neutralization subsystem 115 can operate cooperatively with the sensor subsystem 105 to neutralize the air stream. Controller 117 can sequence operations among the various subsystems, for example, activation and deactivation of the blower subsystem 101 and the power subsystem 111.

Figure 2A:
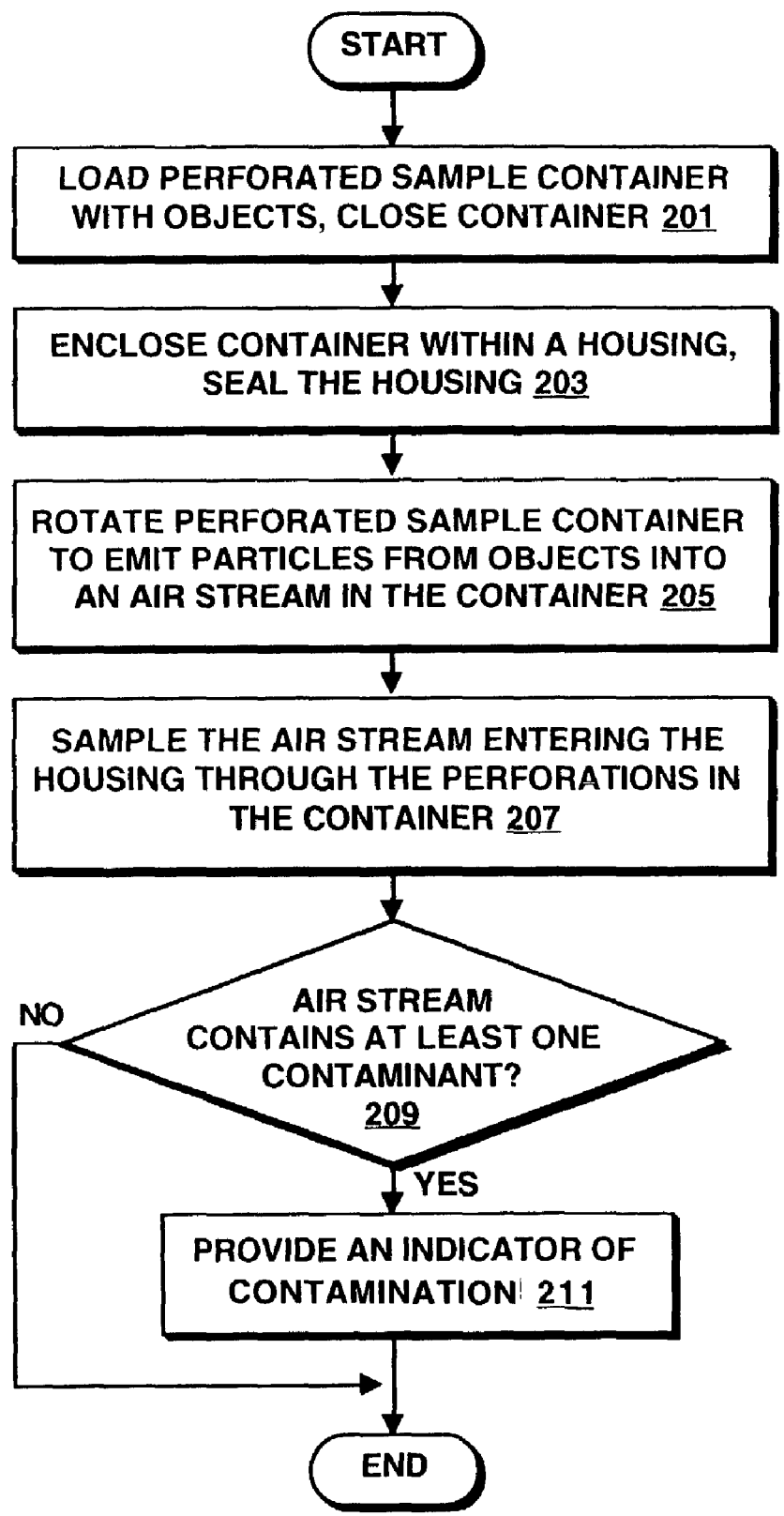
FIGS. 2A and 2B are flowcharts of the method of the illustrative embodiment of the present invention.

Referring now to FIG. 2A, the method of the present invention includes the step of loading a perforated container with objects and closing the container (method step 201). The method further includes the steps of enclosing the perforated container within a housing and sealing the housing to prevent gas exchange between the air inside the housing and the air outside the housing (method step 203). The method of the present invention next includes the step of rotating the perforated container and the objects within the perforated container so that any particles that might on or in the objects are shaken loose by the rotation and emitted into an air stream surrounding the objects within the container (method step 205). The method further includes the steps of sampling the air stream by the sensors for the presence of contaminants (decision step 209), and setting an indicator if at least one contaminant is detected (method step 211).

Figure 2B:
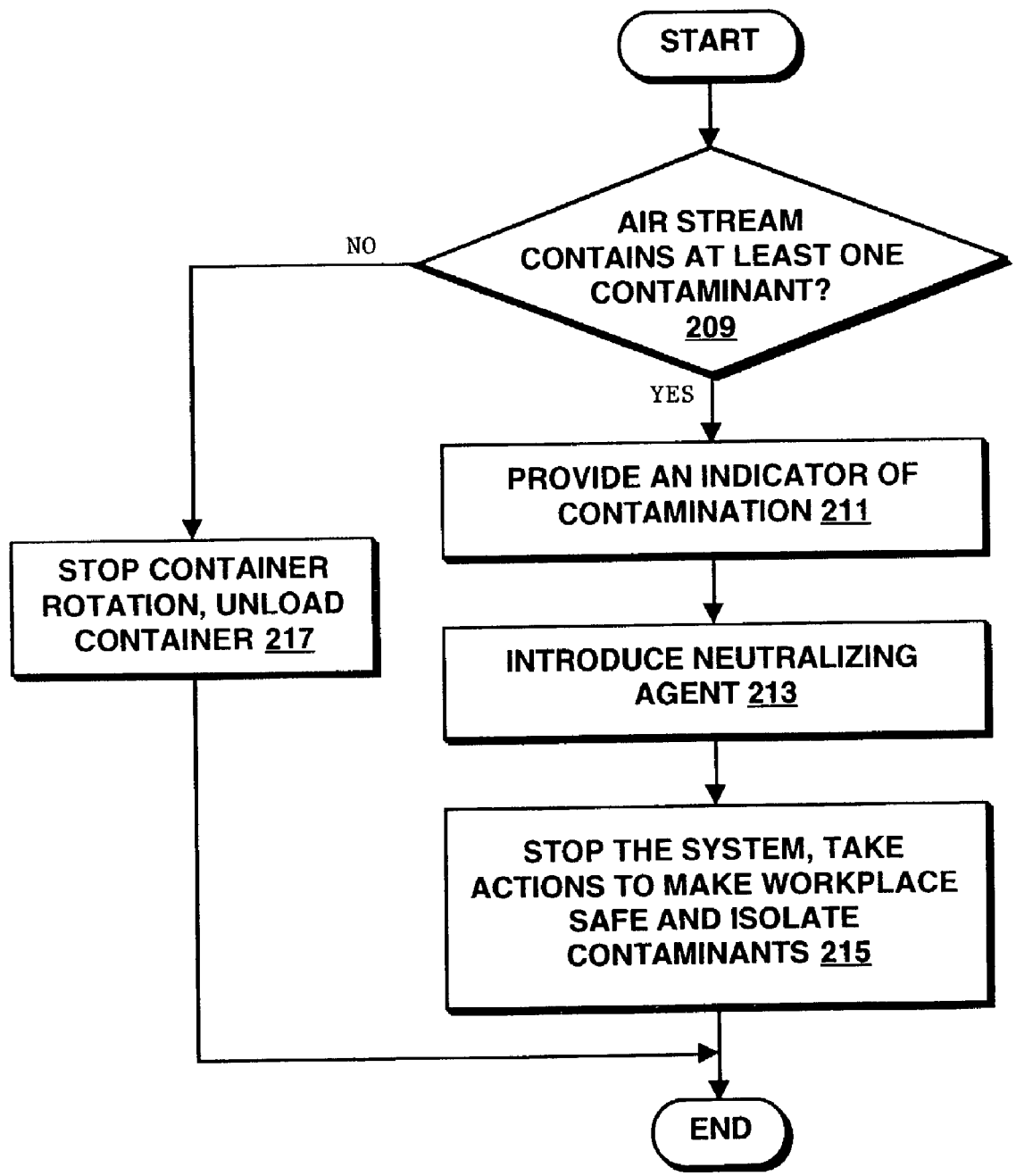

Referring now to FIG. 2B optional steps that can be taken if the air stream contains contaminant(s) include introducing a conventional neutralizing agent into the air stream if at least one active contaminant is detected (method step 213) to neutralize the air stream. The method includes the further step of stopping the system and taking actions to make the workplace safe and to isolate contaminated objects (method step 215). If the air stream is found to be free of contaminants, the method of the present invention includes the final steps of stopping and unloading the perforated container (method step 217).

Figure 3:
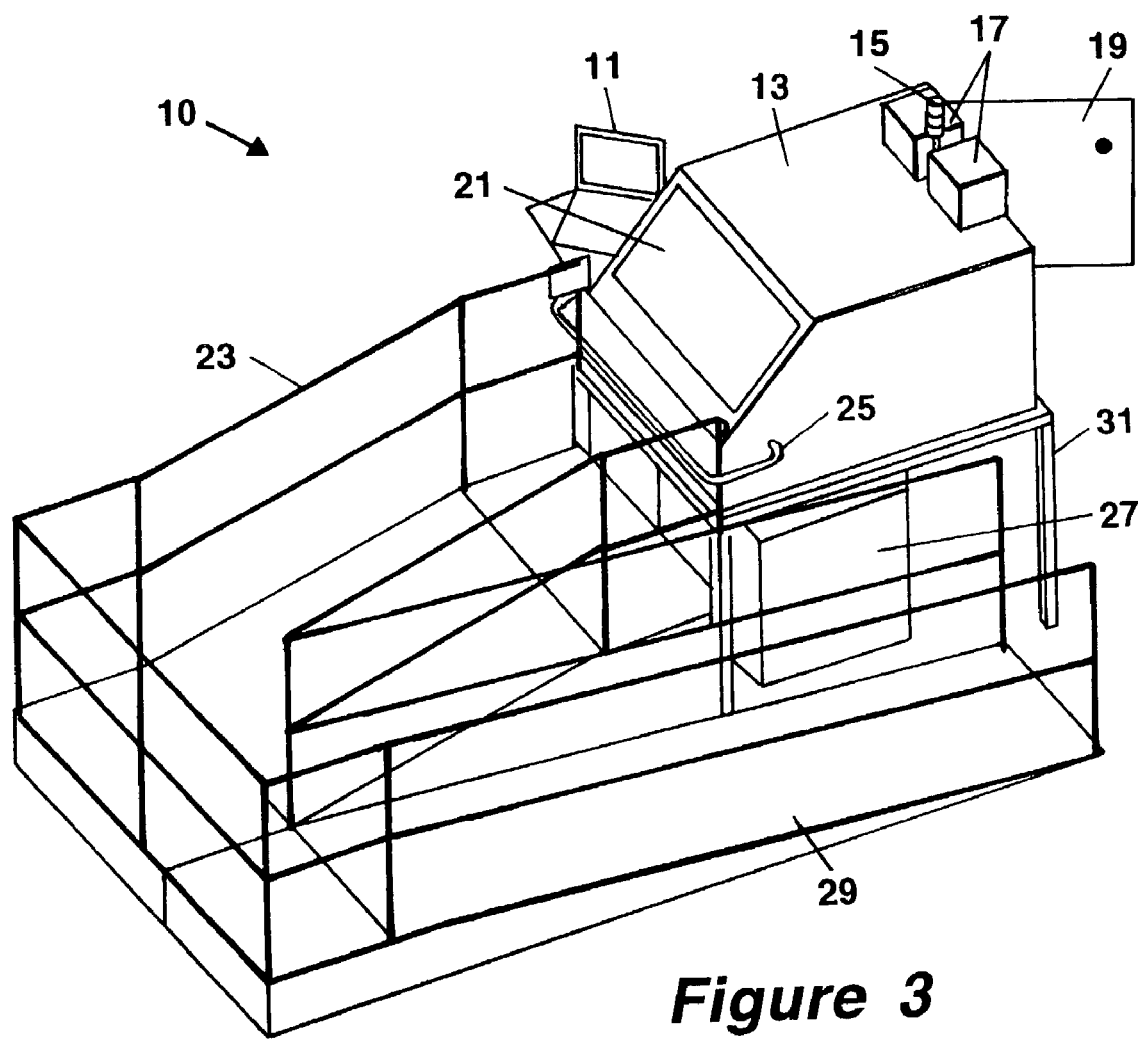
FIG. 3 is a pictorial representation of the illustrative embodiment of the system of the present invention.

Referring now to FIG. 3, system 10 of the illustrative embodiment of the present invention includes housing 13 with housing lid 21 mounted on housing stand 31. In the illustrative embodiment, the housing can be predominately 16–18 gauge stainless steel or any material to allow for corrosion resistance and internal sanitization if necessary. An external framework of powder-coated steel or any other type of material can be used for supporting the housing. The housing can be any size, and could be specially constructed to accommodate certain sizes of objects or areas of application. For example, if the system is to be used primarily in a mailroom, that application could require a relatively large housing to accommodate packages that might be entering the mailroom. On the other hand, if the system were primarily for home use, the housing could be quite small, if desired, to accommodate analysis of flat letters only, for example.

Figure 6:
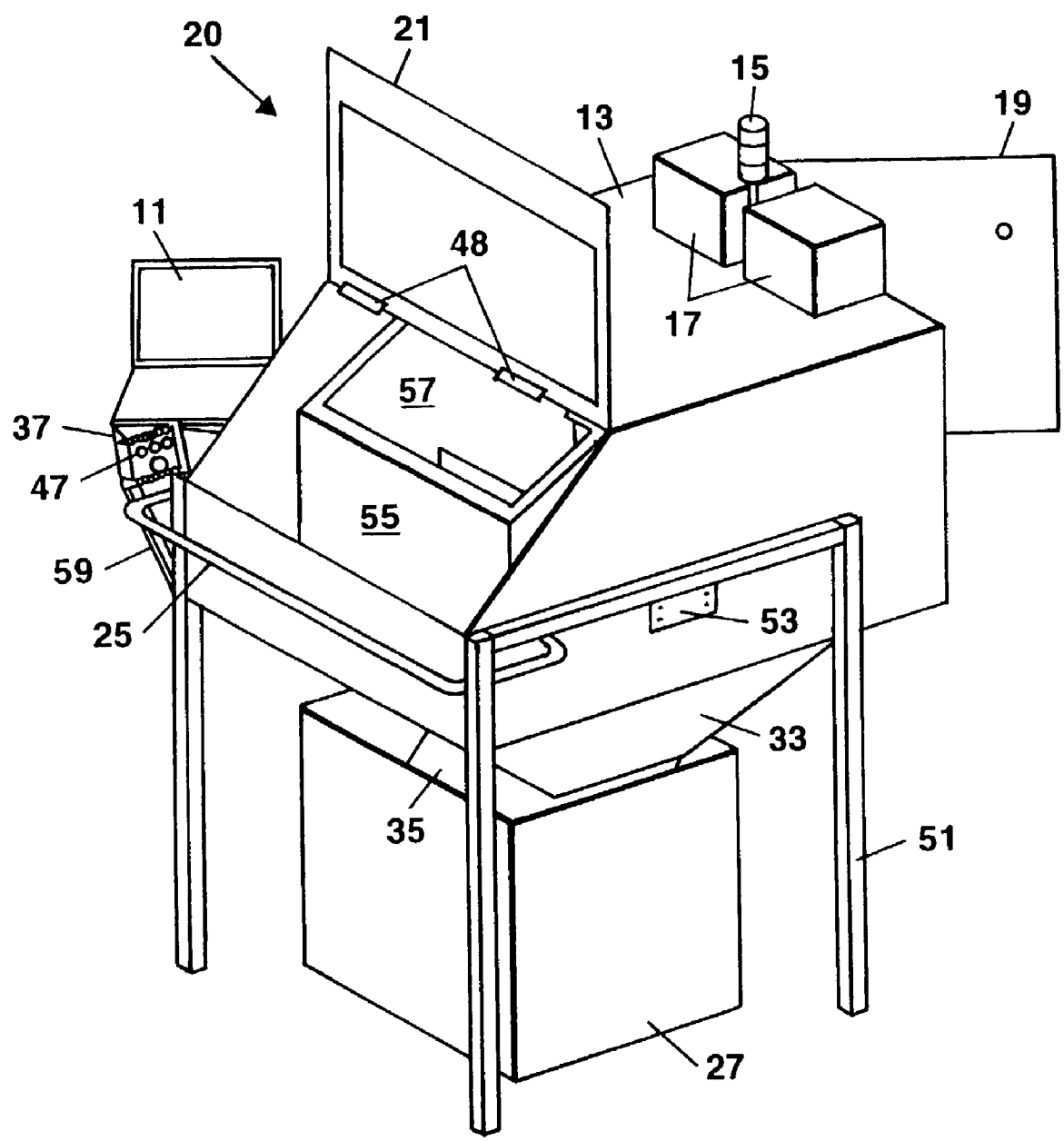
FIG. 6 is a pictorial representation of a front view of the open housing and container of an alternate embodiment of the housing stand of the present invention.

Continuing to refer to FIG. 3, the housing lid 21 is preferably, although not necessarily, a lift-open glass door operably connected to the housing 13 by lid hinges 48 (shown in FIG. 6). System 10 also includes conventional sensors 17 which are, in the illustrative embodiment, a particle sensor and a biological agents sensor, the complementary action of which enhances contaminant detection possibilities. The particle sensing system, illustratively the BAWS I system, is specially suited to detect particles in the 2–10 micron range favored for aerosol dispersion of biologic agents. The biological agents sensor, illustratively the BAWS III sensor, utilizes ultra-violet laser fluorescence technology to analyze captured particles for the presence of biological agents. In the illustrative embodiment, the two sensors can be coupled together by an RS-232 communications line, or any other appropriate electronic communications mechanism. The particle sensor can communicate with a controller 11 through an RF link to the RF radio network or any other suitable means of wired or wireless electronic communications. Note that any sensors, including but not limited to chemical, biological, and particle, can be used in the system of the present invention.

Figure 5:
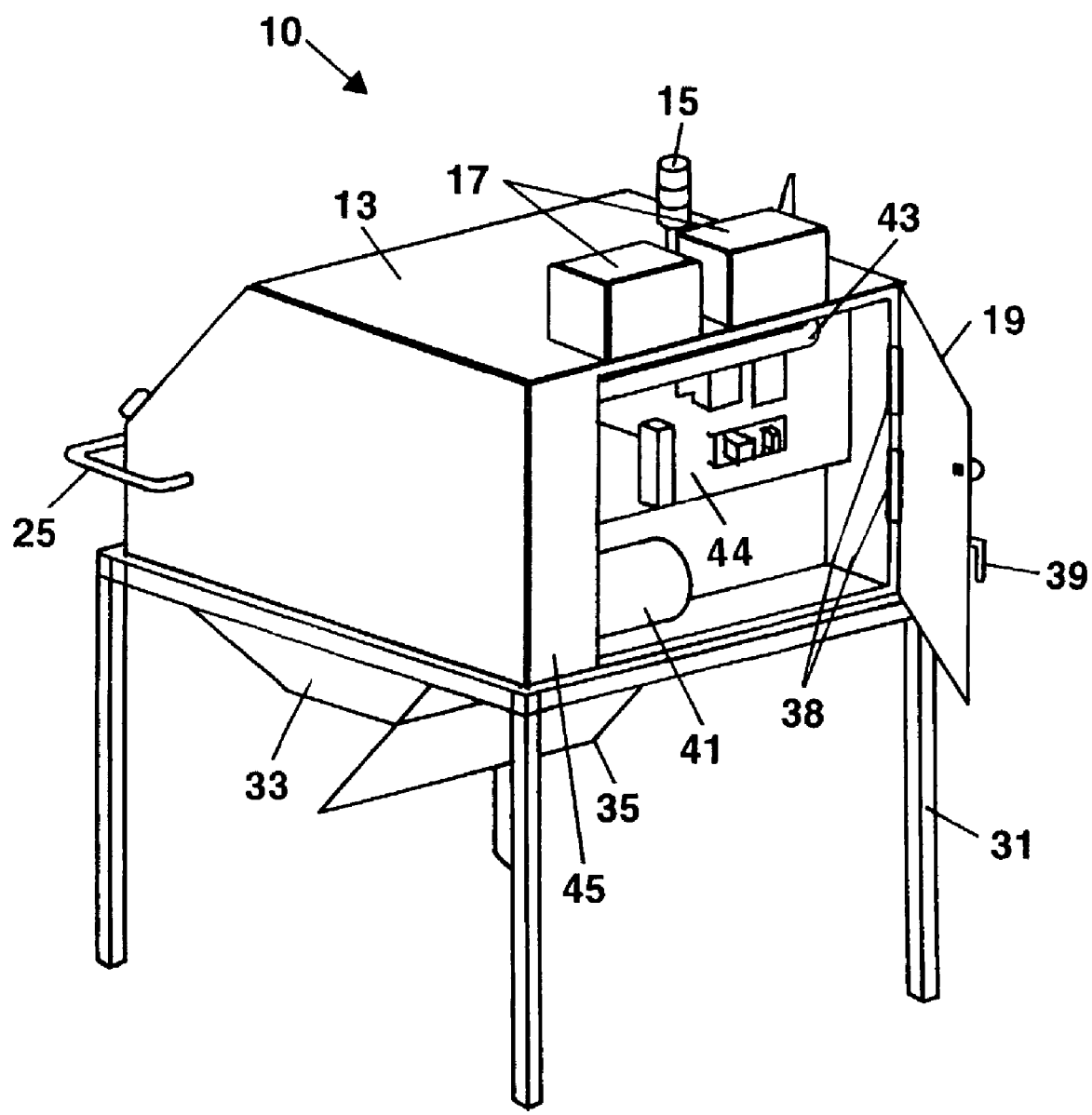
FIG. 5 is a pictorial representation of a rear view of the illustrative embodiment of the system of the present invention.

Continuing to refer to FIG. 3, controller 11, which can be a personal computer, a programmable logic controller, or other such device, is operably connected to interface panel 44 (shown in FIG. 5). In the illustrative embodiment, controller 11 is a personal computer with a Universal Interface Unit for connecting external sensors and an RF network radio. The personal computer of the illustrative embodiment operates under Windows NT, but can operate under any operating system that supports the appropriate hardware and software to interface with and control the various components of the system. Application software to control system 10 is standard BAWS sensor software with upgrades as follows: (1) a new communications message format is added to accommodate information from the sensors of system 10, and (2) the software is modified for non-military use. Any application software appropriate for the sensors selected for the system can be used.

Continuing to refer to FIG. 3, system 10 can also contain a visual indicator 15, an illustrative embodiment of the indicator subsystem 113, that can be color-coded to indicate contamination states. System 10 also includes a rear housing door 19 through which the operator can access the interface panel 44 but which does not allow gas exchange with the air-sealed environment of the housing 13. System 10 also can optionally include discharge handle 25 and discharge receptacle 27. Discharge handle 25 can be pressured manually to release objects from the container 55 (shown in FIG. 6) and housing 13 into discharge container 27, which can be any container suitable for the weight and size of the objects being tumbled in container 55. The handle 25 and housing 13 are operably connected by an interlocking conventional mechanical linkage having a conventional camming feature that reliably seals the discharge hatch lid 35. The conventional interlocking mechanism insures that so that the housing 13 is incapable of being opened during use. It's envisioned that this could be used manually or could be run off the control system and could a pneumatically- or electrically- or hydraulically-controlled, so manual intervention is required. In the illustrative embodiment, an optional loading ramp 29 is shown, having ramp rails 23 and leading to the housing 13. The loading ramp 29 can aid in transporting objects to and loading objects into housing 13.

Figure 4:
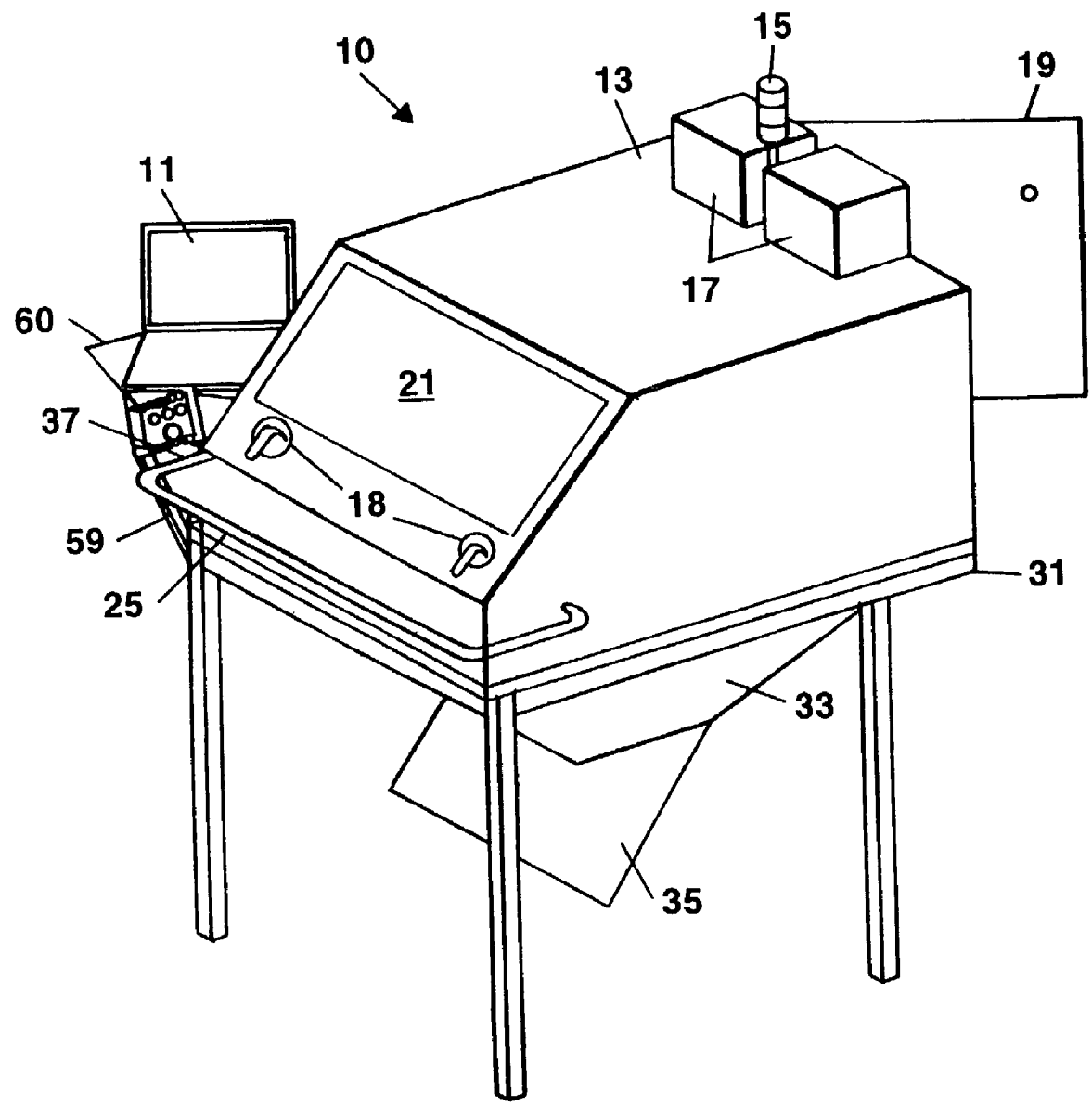
FIG. 4 is a pictorial representation of a front view of the illustrative embodiment of the system of the present invention.

Referring primarily now to FIG. 4, a front view of the housing 13, housing stand 31 and controller 11 are shown. In the illustrative embodiment, controller stand 60, mounted on controller shelf support 59, is operably connected to housing 13 and housing stand 31. Controller 11 can be located any distance from housing 13, but must have electronic (wired or wireless) connection with interface board 44 (shown in FIG. 5). Also shown is control panel 37 which, in the illustrative embodiment, is a panel with start, stop, load/unload, and emergency stop buttons. Also shown are housing lid latches 18 that insure that the housing is sealed against gas exchange with the ambient workspace. Also shown are housing recess 33 and housing discharge lid 35. Housing recess 33 is formed to allow free rotation of container 55. Housing discharge lid 35 is operably connected to handle 25 such that when handle 25 is depressed, after housing discharge lid 35 is opened and the removable lid (not shown) is removed from container 55, container 55 rotates into discharge position and the objects within container 55 drop into receptacle 27.

Figure 8:
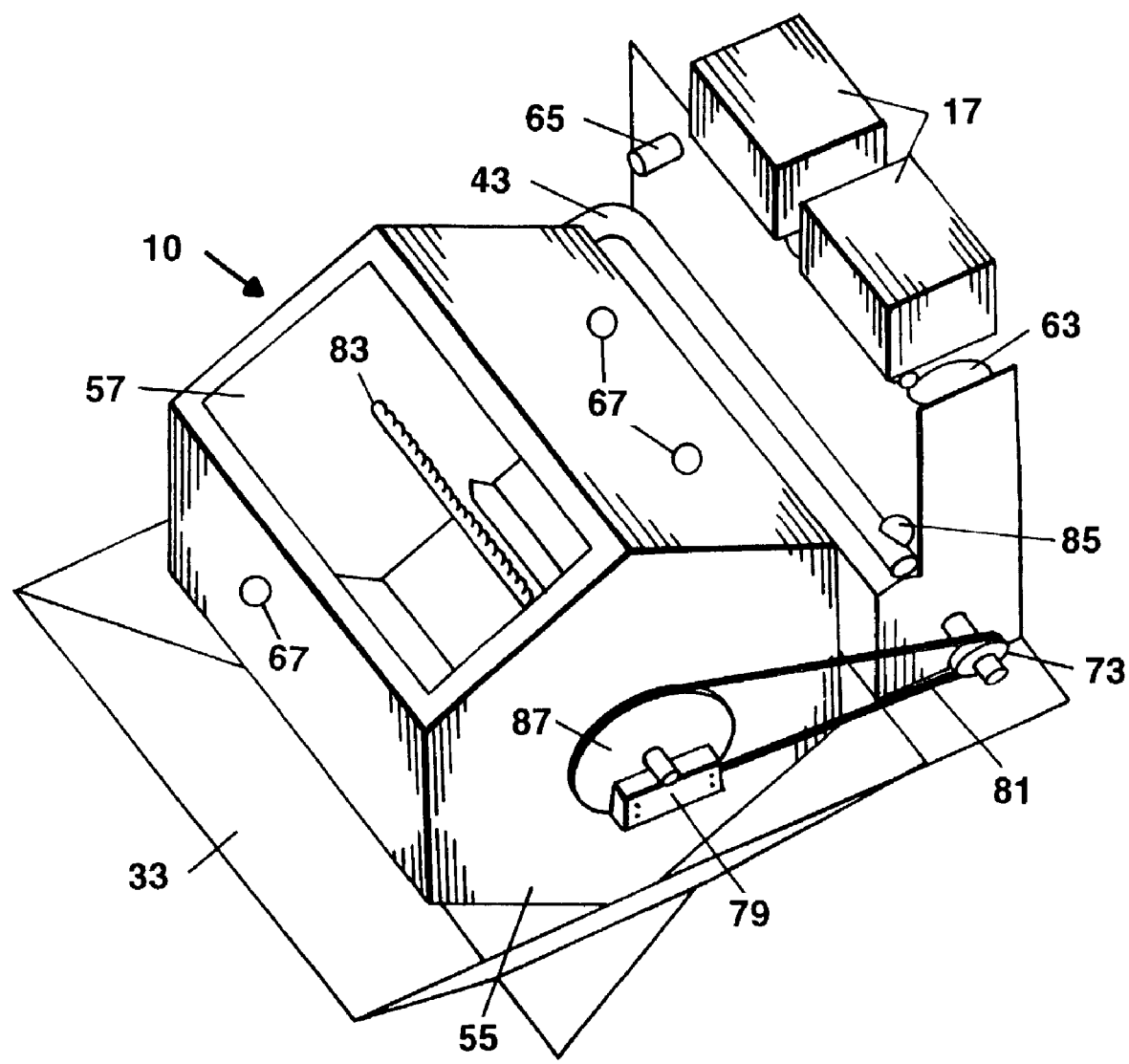
FIG. 8 is a pictorial cut-out representation of a front view of the perforated container and interface board of the illustrative embodiment of the present invention.

Referring now to FIG. 5, a rear view of housing 13, housing stand 31, and interface panel 44 are shown. In the illustrative embodiment, interface panel 44 includes electronics to provide the interface between controller 11 and operational subsystems of the system of the present invention. For example, controller 11 allows the operator to stop the rotation of container 55 through a push-button on control panel 37. Interface panel 44 contains electronics to disable power to motor 41, which thus disables rotation of container 55 (the coupling of motor 41 to the rotation of container 55 is shown in FIG. 8).

Continuing to refer to FIG. 5, rear housing wall 45, along with interface panel 44, complete the rear sealed housing. Interface panel 44 is covered during operation by rear door 19 which can be operably connected to the housing 13 by rear hinges 38 and latched in place by latch 39. Shown also is a pipe of the air duct subsystem 43. This part of the piping ducts air from the housing 13 to the recirculation blower 63 (shown in FIG. 7).

Referring now to FIG. 6, an alternate embodiment 20 of the system of the present invention shows a housing stand in which the housing 13 is supported by attached legs 51 and housing support connectors 53. Also shown (and the same in both illustrative and alternate embodiments) is the perforated container 55 and cavity 57.

Figure 7:
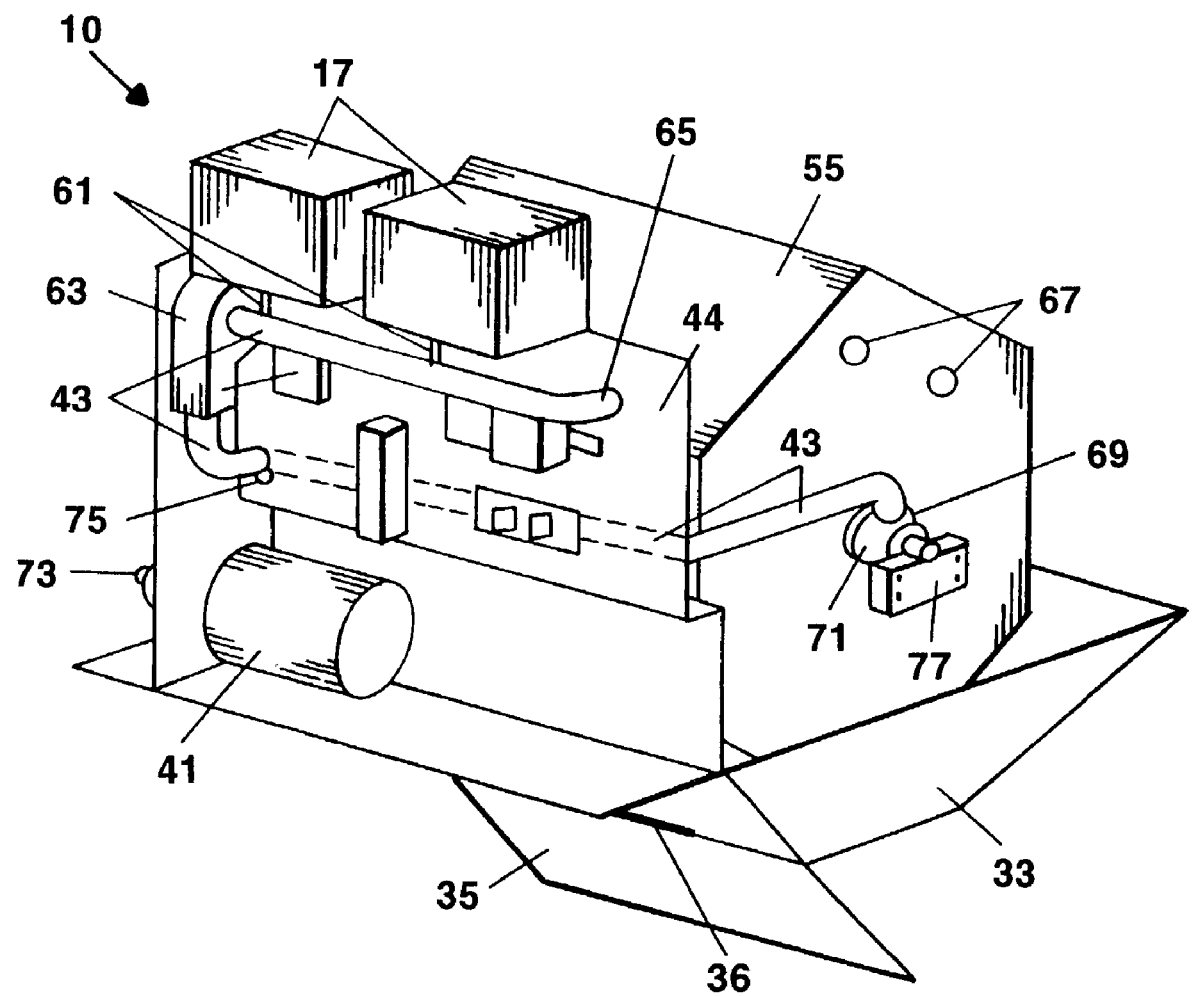
FIG. 7 is a pictorial cut-out representation of a rear view of the interface board and perforated container within the housing of the illustrative embodiment of the present invention.

Referring now to FIG. 7, a rear view of interface panel 44 and container 55 are shown with the housing removed. Container 55, which can be any shape, is six-sided in the illustrative embodiment. It has a removable lid (not shown, attached conventionally when in place) which, when opened, can admit objects into container 55 to be tumbled. Once loaded, container 55, perforated with one or more perforations 67, can be rotated to tumble the objects and agitate them. The preferred rate of rotation is sufficient to tumble the objects in container 55, but not so fast that the objects are pinned to the sides of container 55, thus preventing agitation. The air duct subsystem 43 directs an air stream at the objects within the container by means of a perforated air pipe 83 (shown in FIG. 8) that also acts as an axle to the rotating container 55. Air pipe 83 is in airflow communication with the air duct subsystem 43 which junctions with air pipe 83 at intersection 69. Rotating coupling 71 provides a rotatable connection between the air duct subsystem 43 and the container 55 by allowing the air stream to flow through the coupling 71 while the coupling 71 and the container 55 rotate. Container 55 is attached to housing 13 on one side by air duct housing mounting connection 77.

Continuing to refer to FIG. 7, motor sprocket 73 which drives, for example, a chain, belt, or direct drive that acts as a container rotation means to rotate the container 55 is shown. Also shown is recirculating blower 63 which forces the air stream through the air duct subsystem 43. It can be seen that air leaving container 55 at exit port 65 passes sensor probes 61 on its way to recirculation blower 63. As long as power is supplied to the system, recirculation blower 63 forces the air stream back through interface panel 44 at air duct housing entry 75 and into container 55 at rotating coupling 71. If contamination is detected by conventional sensors 17 through air stream sampling by sensor probes 61, a signal is sent to the indicator subsystem and to controller 11 through interface panel 44.

Referring now to FIG. 8, a front view of container 55 is shown with the housing removed. In this view, container sprocket 87 and chain or belt 81 are shown. Motor 41 (shown in FIG. 7) drives the rotation of motor sprocket 73 and thus drives chain 81 and container sprocket 87 to rotate container 55. Container 55 is connected to housing 13 on the motor side by chain or belt drive housing mounting connection 79. Air duct junction 85 is shown by which the air stream is provided by the recirculation blower 63 at air duct housing entry 75 (shown in FIG. 7).

Figure 9:
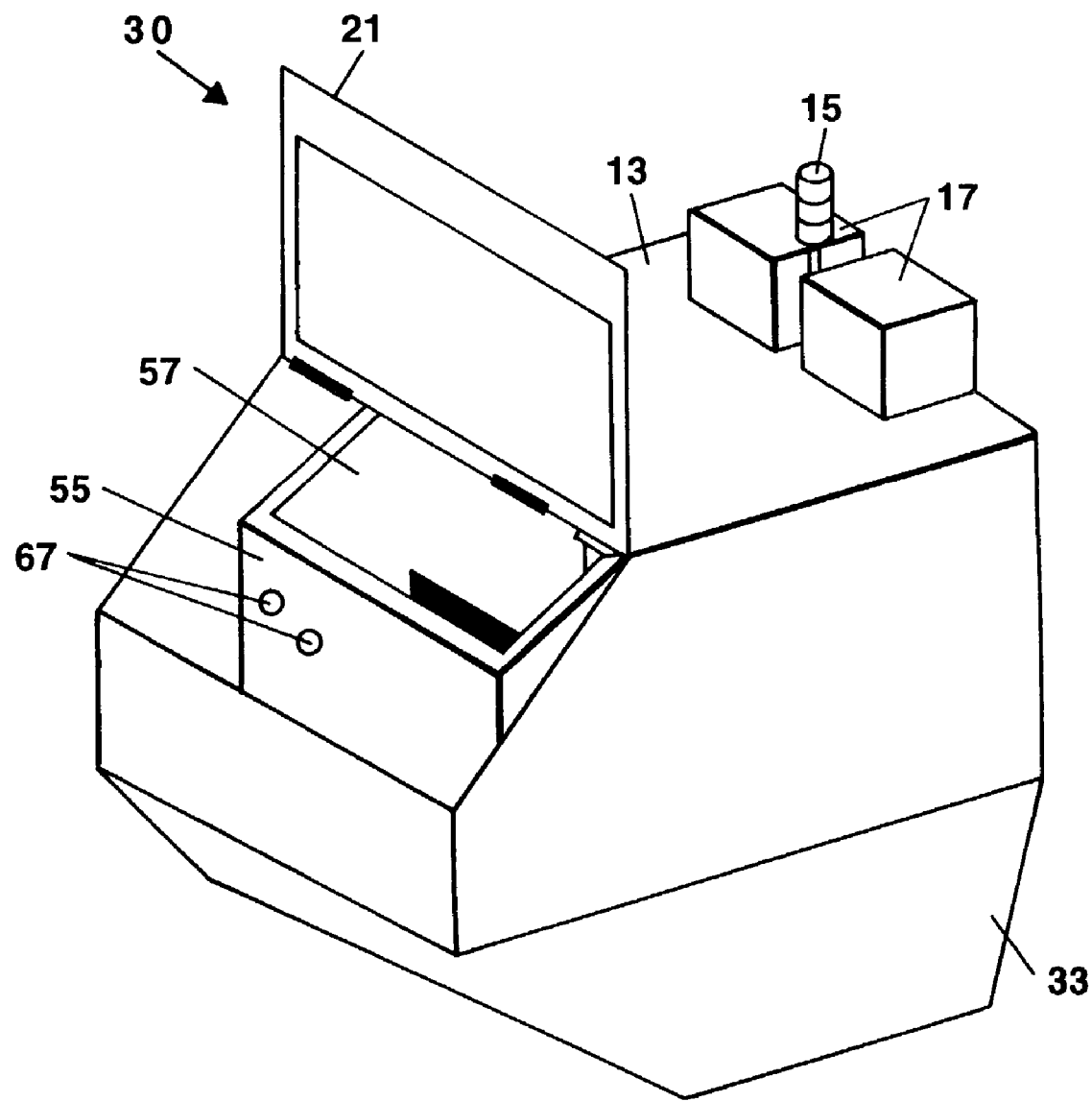
FIG. 9 is a pictorial representation of a second alternate embodiment of the present invention in which the sensors and indicator are directly sensing the air stream in the housing.

Referring now to FIG. 9, second alternate embodiment 30 is shown in which conventional sensors 17 directly sample air inside recessed (reference number 33) housing 13 and provide a first signal to indicator 15 if at least one contaminant is detected. System 30 further includes container 55 which is a six-sided perforated (reference number 67) container that forms cavity 57. Cavity 57 is loaded with objects and then closed as a lid (not shown) is positioned atop container 55. After the objects are loaded, housing lid 21 is shut to prevent gas exchange between the air within housing 13 and the ambient air. Container 55 is rotated by any kind of conventional power supply (not shown), thus tumbling the objects within cavity 57 and perhaps releasing particles associated with the objects into the air in the cavity 57. Air and particles mix and exit cavity 57 through perforations 67 into the enclosure formed by housing 13 where the air and particles are tested for contamination by conventional sensors 17.

Figure 10:
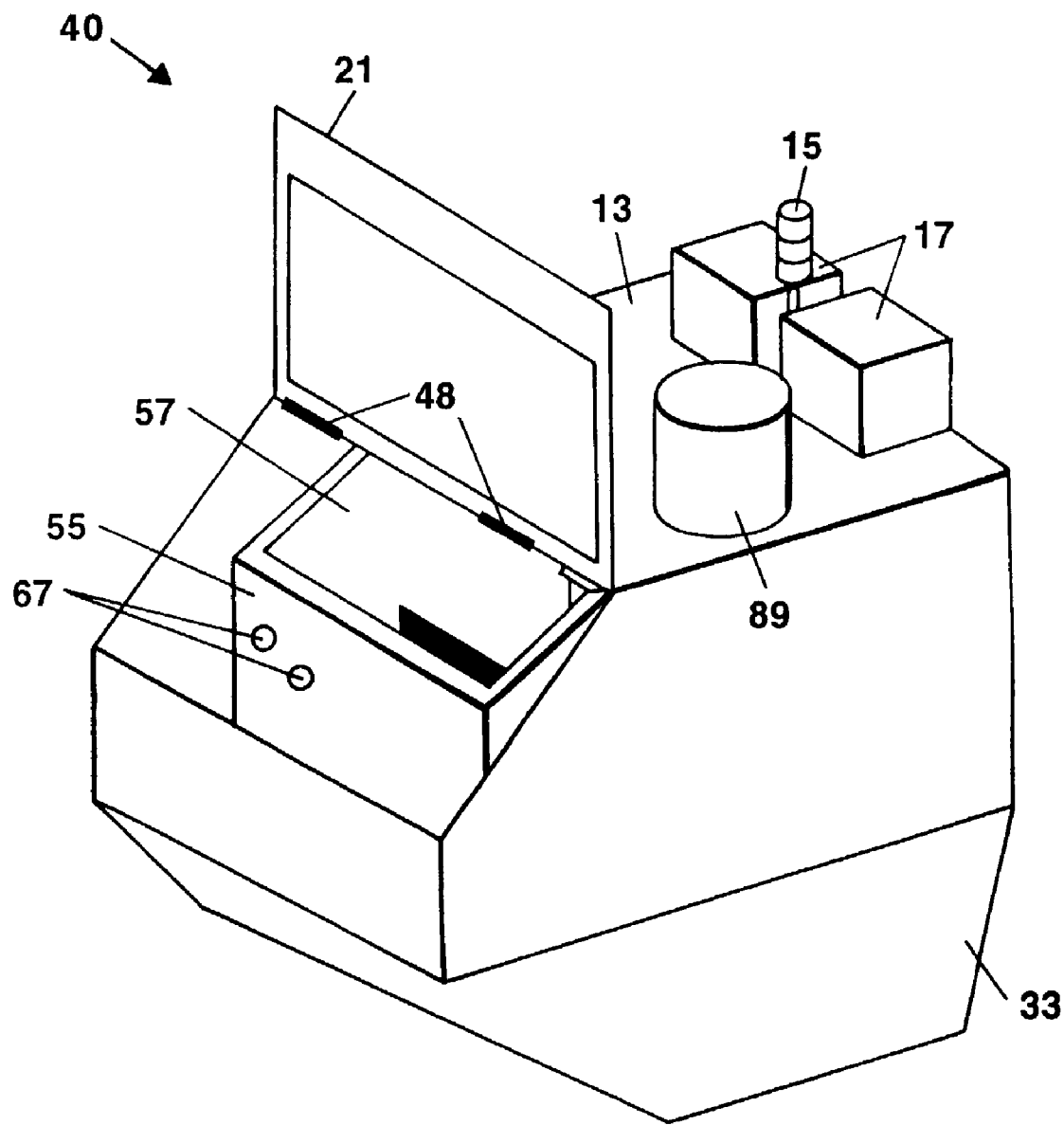
FIG. 10 is a pictorial representation of a third alternative embodiment of the present invention in which the blower, sensors, and indicator, are blowing an air stream directly into the housing and directly sensing the air stream in the housing respectively.

Referring now to FIG. 10, third alternate embodiment 40 in shown which is the same as alternate embodiment 30 except that a conventional blower 89, operably connected to housing 13, forces air into housing 13. The forced air can increase air circulation into container 55 and conventional sensors 17, thus potentially increasing the frequency and reliability of contaminant detection by conventional sensors 17.

Although the invention has been described with respect to various embodiments, it should be realized this invention is also capable of a wide variety of further and other embodiments within the spirit and scope of the appended claims.

What is claimed is:

1. A recirculating method for detecting contaminants in and around at least one object, comprising the steps of:
    loading a perforated container with a plurality of objects;
    enclosing said perforated container within a housing forming an ambient air barrier;
    providing an air stream;
    rotating said perforated container for causing said objects to emit particles which may be thereon or therein into the air stream;
    sampling said air stream;
    testing the sampled air stream for contaminants at a testing location; and
    providing an indication when a contaminant is detected;
    removing any contaminants in the air stream;
    recirculating the air stream to again entrain particles emitted from the objects;
    said air stream being provided to the center of the container where it entrains emitted particles and the air stream is directed past the testing location and the air stream is then redirected to the center of the container.

2. The method of claim 1 further comprising the step of:
    introducing a neutralizing agent into said air stream if said at least one contaminant is detected.

3. A self-contained closed system for detecting contaminants on an object, comprising:
    a. a rotatably mounted container for holding a plurality of objects and having a plurality of perforations and an opening for inserting and removing objects;
    b. a housing enclosing said container and forming a barrier to ambient air and having a sealable opening for inserting and removing objects from said container;
    c. a power subsystem for rotating said container to tumble objects therein to emit particles on or in such objects;
    d. an air moving subsystem for providing an air stream for moving air through said housing and container to entrain any emitted particles into the air stream;
    e. a sensor for sensing contaminants in the air stream and providing a signal when a contaminant is sensed;
    f. a recirculating system for cleaning the air stream of any contaminants after passing the sensor and directing the air stream to again move through the housing and container to again entrain emitted particles into the air stream;
    the air moving subsystem including an air duct system which provides the air stream to the center of the container where it entrains emitted particles and directs the air stream past said sensor and then redirects the air stream to the center of the container.

4. The system of claim 3 wherein said sensor comprises:
    at least one real-time sensor to sense said at least one contaminant, said contaminant being selected from the group consisting of biological particles, chemical particles, and pathogens.

5. The system of claim 3 further comprising an indicator subsystem operably connected to said sensor subsystem for receiving a signal from said sensor subsystem and providing an indication when said at least one contaminant is detected, said indication selected from the group consisting of electrical signal and alarm.

6. The system of claim 3 wherein said power subsystem comprises:
    a motor;
    a motor sprocket operably connected to said motor; and
    a container rotation means operably connected to said motor sprocket, said container rotation means selected from the group consisting of chain and belt.

7. The system of claim 3 wherein said power subsystem further comprises a container rotation means selected from the group consisting of chain, belt, and direct drive.

8. The system as defined in claim 3 further comprising a neutralization assembly for injecting a contaminant neutralizer into the air stream when said sensor detects a contaminant.

9. The system as defined in claim 8 wherein said air moving subsystem directs the air stream from the center of the container through the perforations in the container and into the housing.

10. A system for detecting contaminants in and around a plurality of objects, said system comprising:
    a housing forming an enclosure for providing a barrier to ambient air flow and having a first object opening for inserting and removing objects;
    a container forming a cavity for holding objects and having a plurality of perforations and being rotatably mounted within said housing and having a second opening for inserting and removing objects;
    a blower subsystem for creating an air stream in said cavity;

a power subsystem operably connected to said container for rotating said container so that the objects may emit particles when being tumbled within said cavity when said container is rotated, whereby emitted particles pass through said perforations from said cavity to the air stream;

a sensor subsystem in fluid communication with said enclosure for testing the air stream for at least one contaminant and providing a first signal when a contaminant is detected; and an indicator subsystem operably connected to said sensor subsystem for receiving said first signal from said sensor subsystem and providing a warning signal when said a contaminant is detected in the said air stream;

said blower subsystem including an air duct assembly for ducting said air stream in a closed loop and ducting said air stream into said container, whereby the perforations allow the air stream to enter the enclosure, and the emitted particles are entrained into said air stream, said air duct assembly receives said particles within said air stream and ducts said particles within said air stream past said sensor subsystem, and said sensor subsystem provides a second signal to said indicator subsystem when said contaminant is detected in said air stream;

the blower subsystem air duct system providing the air stream to the center of the container where it entrains emitted particles and directs the air stream past said sensor and then redirects the air stream to the center of the container.

11. The system of claim 10 wherein said blower subsystem comprises a recirculation blower.

12. The system of claim 11 further comprising:
a neutralization mechanism capable of injecting a contaminant neutralizer into said air duct assembly when said sensor subsystem detects said at least one contaminant.

13. The system of claim 10 further comprising:
a controller capable of sequencing operations between said power subsystem and said sensor subsystem.

14. The system of claim 13 wherein said controller is selected from the group consisting of a personal computer and a programmable logic controller.

15. The system of claim 13 wherein said controller is capable of sequencing operations among said power subsystem, said sensor subsystem, and said blower subsystem.

16. The system of claim 13 wherein said housing further comprises:
at least one wall having a recess, said recess being sufficiently sized to accommodate rotation of said container; and
a lid sized to cover said housing opening.

17. The system of claim 13 further comprising:
a neutralization subsystem and said controller is capable of sequencing operations among said power subsystem, said sensor subsystem, said blower subsystem, and said neutralization subsystem.

18. The system of claim 17 wherein said controller is selected from the group consisting of a personal computer and a programmable logic controller.

* * * * *